United States Patent [19]

Saunders

[11] Patent Number: 4,665,020
[45] Date of Patent: May 12, 1987

[54] FLOW CYTOMETER MEASUREMENT OF BINDING ASSAYS

[75] Inventor: George C. Saunders, Espanola, N. Mex.

[73] Assignee: United States Department of Energy, Washington, D.C.

[21] Appl. No.: 615,486

[22] Filed: May 30, 1984

[51] Int. Cl.$^4$ .................. G01N 33/53; G01N 33/543; G01N 33/544; G01N 33/546
[52] U.S. Cl. ........................................... 435/7; 424/3; 424/7.1; 436/523; 436/528; 436/531; 436/533; 436/534; 436/800; 436/823
[58] Field of Search ................. 435/4, 7, 28, 177, 183; 436/501, 518, 523, 533, 534, 546, 823, 824, 528, 800, 531; 424/88.3, 7.1

[56] References Cited

U.S. PATENT DOCUMENTS

| | | | |
|---|---|---|---|
| 3,654,090 | 4/1972 | Schuurs et al. | 195/103.5 |
| 3,791,932 | 2/1974 | Schuurs et al. | 195/103.5 R |
| 3,939,350 | 2/1976 | Kronick et al. | 250/365 |
| 4,100,416 | 7/1978 | Hirschfeld | 250/461 B |
| 4,272,504 | 6/1981 | Kim et al. | 424/1 |
| 4,305,925 | 12/1981 | Kapmeyer et al. | 424/12 |
| 4,320,087 | 3/1982 | Chau et al. | 422/69 |
| 4,341,865 | 7/1982 | Voss | 435/7 |
| 4,348,374 | 9/1982 | Chau | 424/1 |
| 4,430,263 | 2/1984 | March et al. | 435/7 |
| 4,476,228 | 10/1984 | Huchzermeier et al. | 436/500 |
| 4,476,229 | 10/1984 | Fino et al. | 436/500 |
| 4,510,251 | 4/1985 | Kirkemo et al. | 436/536 |

FOREIGN PATENT DOCUMENTS

0064230 10/1982 European Pat. Off.

OTHER PUBLICATIONS

Steinkamp et al, Scientific Instrumentation, vol. 44, No. 9, Sep. 1973, pp. 1301-1310.
Rembaum et al, Science, vol. 28, 4-25-80, pp. 364-367.
Horan et al, Immunoassays in the Clinical Lab: Fluid Phase Particle Fluorescence Analysis, pp. 185-198, 1979.
Nakamura, Immunoassays in the Clinical Lab: Recent Advances in Immunochemical Fluorescent Analytical Methods, pp. 211-226, 1979.
Steinkamp et al, Cytometry, vol. 2, No. 4, 1982, pp. 226-231.
Gill, Manual of Clinical Immunology; Principles of Radioimmunoassay, edited by R. Freedman, 1976, pp. 169-171.
P. J. Lisi et al., "A Fluorescence Immunoassay for Soluble Antigens Employing Flow Cytometric Detection," Clinica Chimica Acta 120, 171-179, (1982).

*Primary Examiner*—Christine M. Nucker
*Assistant Examiner*—Patricia L. DeSantis
*Attorney, Agent, or Firm*—Joseph M. Hageman; Ray G. Wilson; Judson R. Hightower

[57] ABSTRACT

A method of measuring the result of a binding assay that does not require separation of fluorescent smaller particles is disclosed. In a competitive binding assay the smaller fluorescent particles coated with antigen compete with antigen in the sample being analyzed for available binding sites on larger particles. In a sandwich assay, the smaller, fluorescent spheres coated with antibody attach themselves to molecules containing antigen that are attached to larger spheres coated with the same antibody. The separation of unattached, fluorescent smaller particles is made unnecessary by only counting the fluorescent events triggered by the laser of a flow cytometer when the event is caused by a particle with a light scatter measurement within a certain range corresponding to the presence of larger particles.

18 Claims, 8 Drawing Figures

FLOW CYTOMETER MEASUREMENT OF BINDING ASSAYS

This invention is the result of a contract with the Department of Energy (Contract No. W-7405-ENG-36).

BACKGROUND OF THE INVENTION

The present invention relates generally to a method for measuring binding assays and more particularly to measuring binding assays carried out with different size particles wherein the binding assay sample is run through a flow cytometer without separating the sample from the marking agent.

Flow cytometry methods have been developed over time to a point where a single file stream of cells or particles passes through a laser beam. This laser beam can excite any flourescent chemicals present in or on the particles. The emission of the fluorescent chemicals when struck by the laser and also such other properties as light scatter due to the particles passing through the laser beam are measured by detectors. This technique combined with deflection plates as described in a 1973 article (A New Multiparameter Separator for Microscopic Particles and Biological Cells, Steinkamp, et al., Review of Scientific Instrumentation, Vol. 44, No. 9, Sept. 1973, p. 1301) explained how the fluorescence of the subject cells or particles could be used as a criterion to separate them. The article also described the use of uniform plastic microspheres to evaluate the combined methods.

Immunoassay techniques are based upon well known reactions between an antibody and the specific antigen or hapten for that antibody. Often one component is tagged, sometimes with a radioactive isotope or sometimes with a fluorescent tracer material, to quantify the percentage of reagent coming from a sample of unknown composition as compared with a known amount of tagged material. U.S. Pat. No. 4,100,416 showed the use of fluorescent tracer material in a competitive binding situation. Competitive binding assays were explained in U.S. Pat. No. 3,939,350. Analysis of the results of the competitive binding assays in U.S. Pat. No. 4,100,416 was by use of a totally internally reflecting cell. In addition to antibodies and antigens, other reacting systems have been used, such as enzyme and substrate for the enzyme, hapten and antibody for the hapten, or a ligand and its receptor. Finally, the use of immunomicrospheres was suggested (Immunomicrospheres: Reagents for Cell Labeling and Separation, A. Rembaum and W. J. Dreyer, Science, Vol. 208, Apr. 25, 1980, p. 364) wherein the immunomicrospheres would be made fluorescent by the addition of the chemical and then bound to larger magnetic beads. Furthermore the article suggested that antibody-coated fluorescent microspheres would attach themselves to antigen previously coated on the wall of the small capillary tube. The bound microspheres would then be eluted and monitored in a fluorimeter.

Problems still remained however with the above methods. Most methods, except for the totally internally reflecting cells, required a step for separating out the unbound, unreacted fluorescent tagged material from the sample before analysis. This separation step proved to be troublesome because the removal of the unreacted tagged material would shift the equilibrium established at the end of the competitive binding process. Aside from the trouble in making sure all the unreacted tagged material had been separated out, the equilibrium shift of the bound tagged material introduced error into the final results. Errors were introduced into the totally internally reflecting cell measurements by the fact that only the tagged cells bound to the wall of the cell would fluoresce when struck by the laser light deliberately confined to the narrow space near the surface of the cell. Additionally, problems were introduced into the measurement technique by the requirement for confining the laser light near the surface of the cell. Finally, a need existed for a method wherein it would be unnecessary to separate the unbound, fluorescent-tagged material from the sample before analysis in a flow cytometer.

SUMMARY OF THE INVENTION

An object of this invention is to provide a method for analysing the results of a binding assay accurately and quickly.

A further object of this invention is to provide for a method of analysis for the results of a binding assay without the necessity for separating out unbound, tagged material.

Another object of this invention is to provide a method for measuring the results of a binding assay without being confined to a reaction surface of a totally internally reflecting cell.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, in accordance with purposes of the present invention, as embodied and broadly described herein, the method of this invention may comprise: determining the amount of a binding reactant present in a sample by providing particles with a coating of binder and also a known quantity of smaller particles with a coating of binder reactant, the binding reactant being the same as the binding reactant present in the sample, the smaller particles also containing a fluorescent chemical; then combining the particles with the sample and allowing the binding reaction to occur for a set length of time; followed by combining the smaller particles with the mixture of the particles and the sample produced in the previous step and allowing the binding reactions to proceed to equilibrium; and then simultaneously measuring the fluorescence and light scatter of the combined mixture of sample, particles, and smaller particles as the combined mixture passes through a flow cytometer equipped with a laser which causes the fluorescent chemical in the smaller particles to fluoresce; and finally comparing the number and strength of the fluorescent events caused by the particles having a light scatter measurement within a predetermined range against similar number and strength of events caused by particles reacted with a sample of known binder reactant percentage.

The present invention may also comprise, in accordance with the objects and purposes, a method for determining the amount of antigen present in the sample by providing spheres with an antibody coating and also a known quantity of smaller spheres with an antigen coating, the antigen being the same as the antigen present in the sample, and the smaller spheres containing a fluorescent chemical; then combining the spheres with the sample and allowing the reaction between the antigen and the antibody on the spheres to occur for a set period of time; then combining the smaller spheres with the mixture of the spheres and the sample produced in the previous step and allowing the reaction between both the remaining antibody on the spheres and the antigen on the smaller spheres and in the sample to proceed to equilibrium; then simultaneously measuring the fluorescence and light scatter of the combined mixture of sample, spheres, and smaller spheres as the combined mixture passes through a flow cytometer equipped with a laser causing the fluorescent chemical in the smaller spheres to fluoresce; and finally comparing the number and strength of the fluorescent events caused by the spheres having a light scatter measurement within a predetermined range against similar events caused by spheres reacted with a sample of known antigen concentration.

The present invention additionally may also comprise, in further accordance with the objects and purposes, a method for determining the amount of molecules containing antigen present in a sample by providing a known quantity of spheres and an excess of smaller spheres, both coated with an antibody, and the smaller spheres containing a fluorescent chemical; then combining the spheres with the sample and allowing the reaction between the antigen contained in the molecules of the samples and the antibody on the spheres to occur for a set time period; then combining the excess of the smaller spheres with the mixture of the spheres and the sample produced in the previous step and allowing the reaction of the antibody on the spheres and smaller spheres with antigen contained in the molecules in the sample to reach equilibrium; then simultaneously measuring the fluorescence and light scatter of the combined mixture of sample, spheres, and smaller spheres as the combined mixture passes through a flow cytometer equipped with a laser causing the fluorescent chemical in the smaller spheres to fluoresce; and finally comparing the number and strength of fluorescent events caused by spheres having light scatter measurements within a predetermined range against similar events caused by spheres with no fluorescent smaller spheres present.

In a preferred embodiment of the invention the spheres are polystyrene and the smaller spheres measure 0.1 $\mu$m in diameter, while the other spheres are 10 $\mu$m in diameter.

By using the method of the invention, a quicker, more accurate measurement of the result of a competitive binding assay is provided. No longer is it necessary to separate out reacted, tagged material before measurement by flow cytometry. Eliminating fluorescent events for particles with light scatter measurements outside a specified range prevents distortion of the results by fluorescence of unreacted, unbound smaller particles or spheres. Thus, it is not necessary to disturb the equilibrium reached at the end of the competitive binding assay process before measurement with the inevitable distortion of the measurement of bound, tagged smaller spheres.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 5 is a graph of net fluorescence versus HRP molarity for a standard sandwich assay curve.

DETAILED DESCRIPTION OF THE INVENTION

Figure 1A:
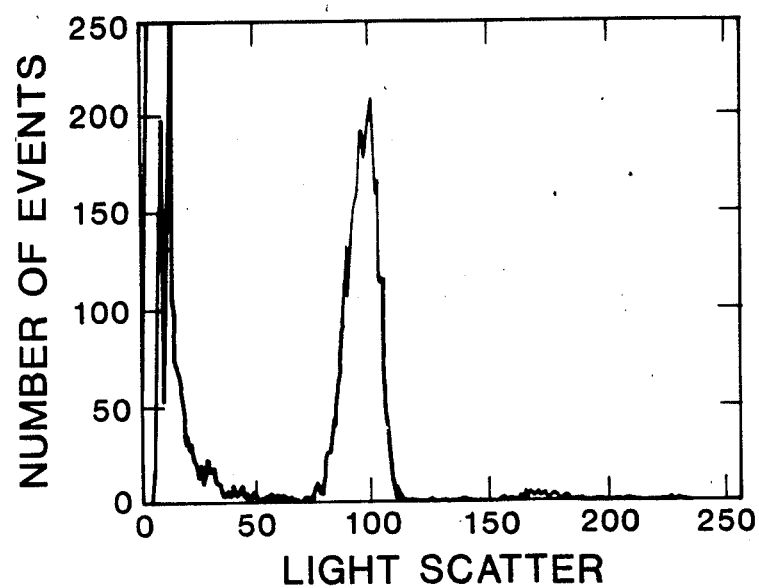
FIG. 1a is a graph of computer reprocessed data showing the number of events versus light scatter for 10 $\mu$m particles in Example 1 where no soluble HRP is added.

In order to carry out the competitive binding assay for later analysis by flow cytometry, some type of particles, preferably uniform spheres, are needed. Latex spheres made of polystyrene of two different diameters are available from Dow Chemical Co., Polysciences, Inc., and other companies. The smaller diameter spheres should be tagged with a monomer such as dansyl allylamine or an adduct of allylamine and fluorescein isothiocyanate. The particles may also be made according to the methods in the article: Immunomicrospheres: Reagents for Cell Labeling and Separation, previously cited herein and hereby specifically incorporated by reference. Whichever type of particles are used, the larger diameter particles should be coated with a layer of a binder, such as an antibody coating. The smaller spheres, those containing the fluorescent tagging material, should also be covered with a layer of binder reactant, such as an antigen or an antibody coating. Any excess binder or binder reactant is removed from the spheres before carrying out the binding assay.

To a sample with an unknown concentration of antigen or to a standard with a known concentration antigen which is used to calibrate later results, a known quantity of particles or spheres with antibody coating is added. The binding reaction is allowed to proceed for a set period of time. This allows the antigen in the sample or standard to occupy a percentage of the available antibody-binding sites on the particles or spheres. To this combination of particles and sample is added an excess of smaller spheres containing fluorescent tagging material. The binding reaction for this combined mixture of particles or spheres, smaller particles or spheres, and sample or standard is allowed to proceed to equilibrium. The combined mixture is now ready for flow cytometry analysis, without the necessity of separating out the unreacted antigen or antibody coated fluorescent smaller spheres. Skipping this step represents not only a saving of labor and expense necessary to separate out the excess fluorescent spheres, but also an improvement in accuracy. During any separation step, the equilibrium will be affected, most probably by detachment of antigen, whether it is antigen from the sample or the antigen-coated fluorescent spheres.

A combined mixture of particles, smaller particles, and sample can be analyzed by any number of commercially available flow cytometers. A particularly useful flow cytometer is the FACS II model from Becten-Dickenson equipped with a argon-ion type laser emitting a beam of 457 nm wavelength light. A flow cytometer must not only measure fluorescene of the particles as they pass through the laser beam, but it also must measure the light scatter of the individual particles. Preferably, the detectors for fluorescene and light scatter report to a device that can count the number and strength of fluorescent events caused by particles with a light scatter measurement within a predetermined range. The number and strength of such fluorescent events can then be plotted on a graph where the number of events is arrayed against the events' fluorescent intensity.

A comparison of the graphs of the number of fluorescent events against their intensity is then compared with known standards. One standard to which the graphs from samples with unknown concentration of antigen can be compared is the graph produced by a similar known quantity of antibody-coated spheres wherein a predetermined percentage of available sites on the spheres have been occupied by smaller spheres with an antigen coating and fluorescent tagging, such smaller spheres having been added in the amount known to label, at equilibrium, 40-60% of sterically available binding sites on the larger spheres. Because the antigen in the sample with an unknown concentration of antigen does not have a fluorescent chemical tag added, the fluorescence of the competitive binding assay should be affected in portion to the amount of the antigen from the sample. This will be reflected upon the graph by a leftward shift of the peak of the plot of the number of fluorescent events versus the fluorescent intensity. The degree of leftward shift obtained in a series of standard samples containing known concentrations of antigen can be used to calculate the number of sites on the spheres which were occupied by antigen from the sample instead of the antigen attached to the fluorescent microspheres.

In a sandwich immunoassay for protein antigens which have multiple binding sites for antibody, antibody is coated onto both the large and small spheres. The sequence of the assay steps in a sandwich assay is the same as for a competitive binding assay. However in a sandwich assay the fluorescence of the large spheres is directly proportional to the concentration of soluble antigen (protein) present in the reaction mixture, where the converse is true in a competitive binding assay. In a sandwich assay, rather than competing for available sites remaining on the larger particles, the antibody coated smaller particles bind to the soluble antigen which has been bound to the larger particle; hence the more antigen bound, the greater the number of fluorescent smaller particles which can be bound. A standard to which the graphs from samples with unknown quantities of antigen can be compared is that produced by a mixture of a known quantity of antibody-coated large spheres and an excess of antibody-coated fluorescent small spheres in the absence of soluble antigen. The nonspecific binding which occurs is reflected in a relatively low mean fluorescence value. As soluble antigen concentration is increased the mean fluorescence value obtained for the figure is shifted to the right. The degree of the rightward shift obtained in a series of standard samples containing known concentrations of soluble antigen can be used to calculate the antigen concentration contained in unknown samples.

The fact that only those fluorescent events to be counted are produced by cells giving a light scatter within a certain range eliminates the need for separation of the unbound, antigen coated or antibody coated, fluorescent microspheres that are not attached to the larger spheres or molecules respectively. Because of the size difference between the antigen or antibody coated smaller spheres and the antibody-coated spheres, the light scatter readings will differ. By selecting only those fluorescent events that are produced by spheres with a light scatter reading with a certain range that corresponds to the light scatter from spheres with a larger diameter, the fluorescent events from spheres with a smaller diameter are not counted, and hence not shown on the graph of fluorescent events versus fluorescent intensity. Thus, the graph is constructed from data that is not influenced by the presence of the smaller spheres that have not attached themselves to the larger spheres or molecules of the sample.

EXAMPLE I

A standard competitive binding assay curve was obtained by the following process. One milliliter of 5% BSA-PO$_4$ buffer, PH 8.2, was added to each of a series of 12×75 mm polypropylene tubes (Falcon 2063). After sitting at room temperature for at least 30 minutes serial log (base 10) dilutions of antigen were made from a $10^{-5}$ molar horseradish peroxidase (HRP) stock solution. One tube in each series received no HRP. To each tube $10^5$ (in 50 μl) HRP antibody coated 10 μm spheres were added. The reaction between HRP in solution and antibody coated spheres proceeded for time $T_1$ (24 hrs.). Then 30 μl of a 0.005% suspension of 0.1 μm diameter HRP coated particles were added for time $T_2$ (16 hrs.). Then a portion of the reaction mixture was analyzed in a Becten-Dickenson FACS II Cell Sorter for both light scatter and fluorescence. In each tube measurements on at least 3000 large particles where made by the flow cytometer. The instrument gain settings were set up up from a tube containing only antibody and antigen coated particles (no soluble HRP) so that a good Gaussian distribution of the 10 μm particles light scatter signal was centered between channels 50-100 on a 256 channel analyzer. Likewise the Gaussian distribution of the fluorescence associated with the 10 μm particles were set to center between channels 100 and 200 on a 256 channel analyzer. The mean of this reprocessed (see below) fluorescence distribution was taken as 100% (or maximum) fluorescence. Then without changing instrument settings or sample flow rates, all tubes in the series were similarly analyzed. All data were computer reprocessed to display only the fluorescence due to single (as compared to doublets, etc) 10 μm particles (FIGS. 1 and 2).

Light scatter and fluorescence data obtained in a competitive binding assay where no soluble HRP was added. Maximum binding of 0.1 μm antigen coated particles occurred in this sample. The light scatter signal of single 10 μm diameter particles is the large distribution centered near channel 95. Signals to the left represent small particulate debris present in the sample while signals to he right (centered about channel 180) represent doublets of the 10 μm spheres.

Figure 1B:
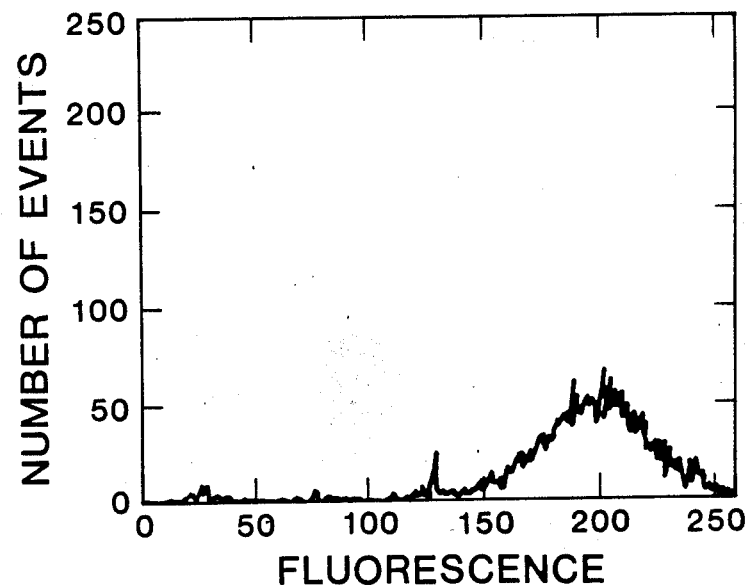
FIG. 1b is a graph of computer reprocessed data showing the number of events versus fluorescence for 10 $\mu$m particles in Example 1 where no soluble HRP was added.
Figure 2A:
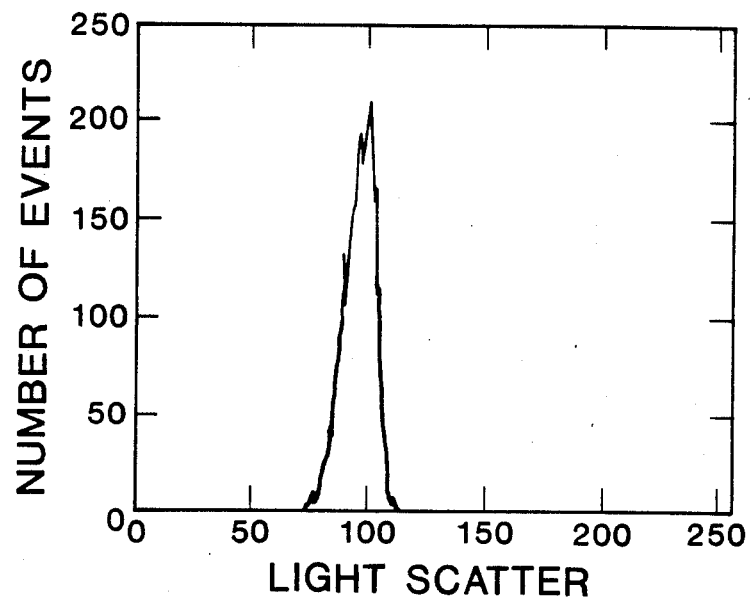
FIG. 2a is a graph of reprocessed data from FIG. 1a in which fluorescence is due only to single 10 $\mu$m particles.
Figure 2B:
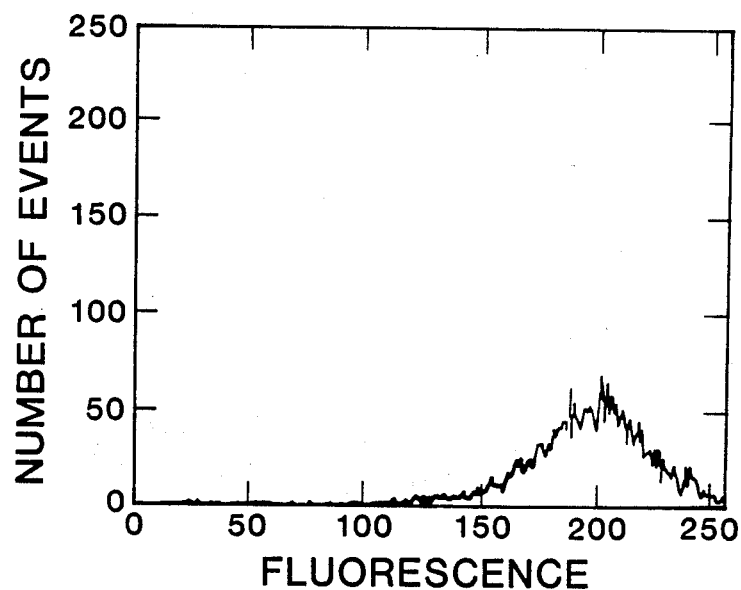
FIG. 2b is a graph of reprocessed data from FIG. 1b in which fluorescence is due only to single 10 $\mu$m particles.
Figure 3A:
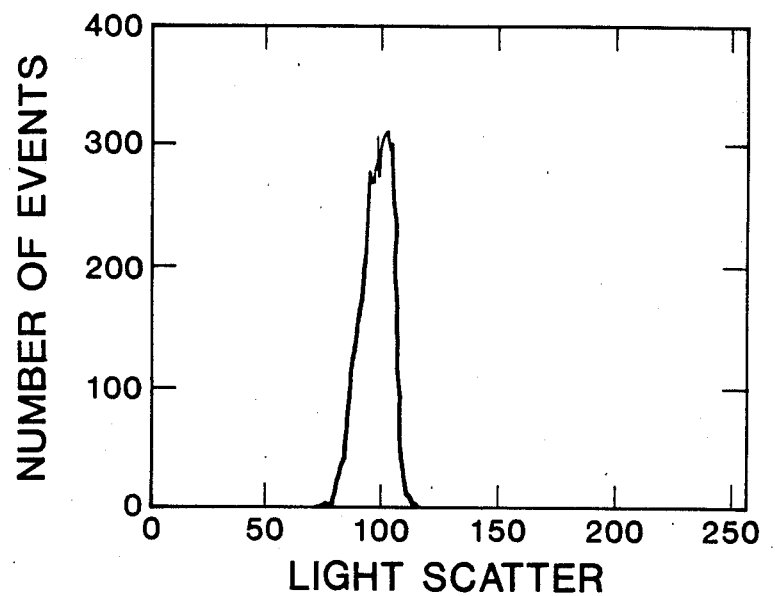
FIG. 3a is a graph of computer reprocessed data showing the number of events versus light scatter for 10 $\mu$m particles in Example 1 where $10^{-10}$M soluble HRP was present.
Figure 3B:
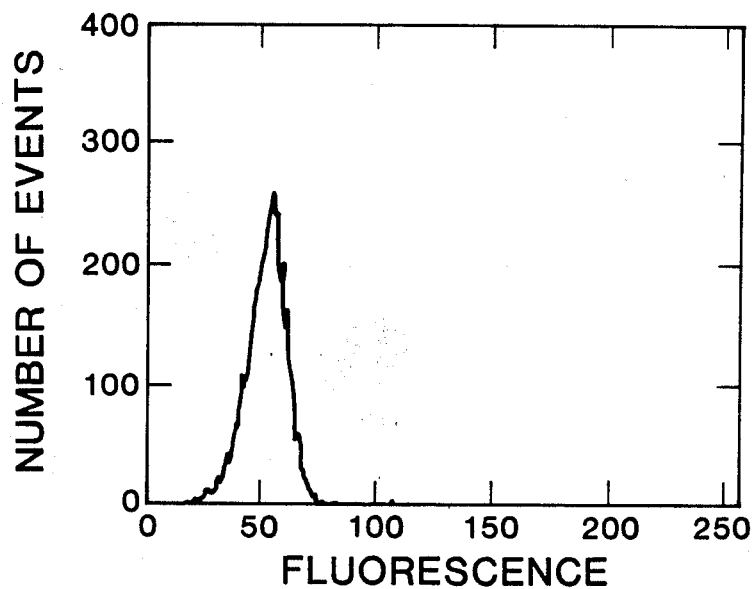
FIG. 3b is a graph of computer reprocessed data showing the number of events versus fluorescence for 10 $\mu$m particles in Example 1 where $10^{-10}$M soluble HRP was present.

Reprocessed data from FIG. 1 in which the fluorescence due only to single 10 μm particles is illustrated. The mean of this fluorescence distribution is taken as maximum (100%) fluorescence. FIGS. 1 and 2 illustrate the type of data obtained in a sample where no soluble HRP was added, while FIG. 3 illustrates data obtained form a sample containing $10^{-10}$M soluble HRP.

Reprocessed data from which contained $10^{-10}$M soluble HRP. As can be seen compared to FIG. 2 the light scatter peak remains relatively constant while the fluorescence peak has shifted markedly to the left. Values of the mean channel of the fluorescence intensity from each sample were converted to percent maximum fluorescence and these values were plotted as a function of HRP concentration (FIG. 4).

Figure 4A:
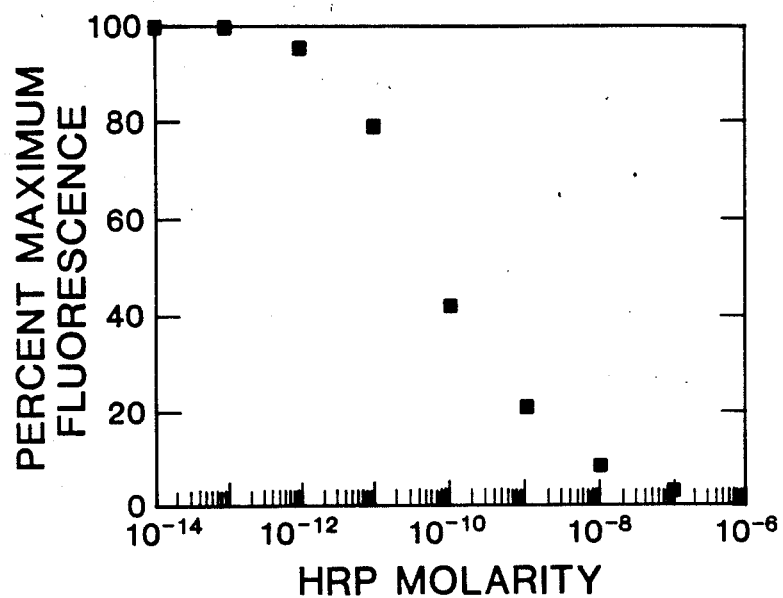
FIG. 4 is a graph of percent maximum fluorescence versus HRP molarity for a standard competitive binding displacement curve.
Figure 4B:
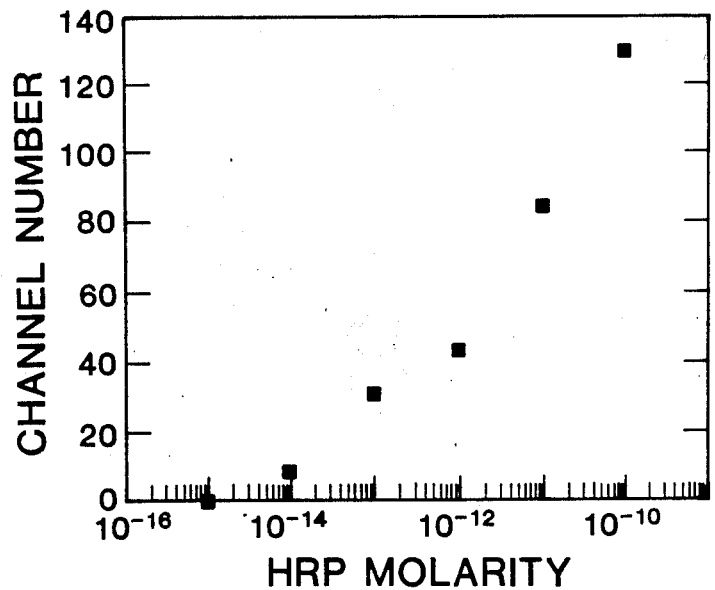

FIG. 4 is that of a standard competitive binding displacement curve obtained from a typical run. The percent maximum fluorescence is plotted as a function of soluble HRP concentration. The assay sensitivity was about $10^{-12}$ molar soluble HRP and the dynamic range of the assay was 5 orders of magnitude. As can be seen, the fluorescence intensity decreases as the concentration of soluble HRP increases due to the competition for available binding sites on the larger particle by the soluble antigen present. In this example assay sensitivity was $10^{-12}$ molar soluble HRP.

EXAMPLE II

Using the same lots of spheres described in Example I, both the large and small spheres were coated with HRP antibody. A standard curve for a sandwich binding assay was obtained by the following process. Standard log dilutions of soluble HRP were made as in Example I. To each tube, $10^5$ (in 50 μl) HRP antibody-coated 10 μm spheres were added. The reaction between HRP in solutions and antibody coated spheres proceeded for 24 hrs ($T_1$). Then 25 μl of a 0.025% suspension of HRP antibody coated 0.1 μm spheres were added for 7 hrs ($T_2$). Then a portion of the reaction mixture was analyzed for light scatter and fluorescence as in Example I. The instrument gain settings were set up from a tube containing both diameters of HRP antibody containing spheres, but no soluble HRP, so that the distribution of the 10 μm particle light scatter signal was centered between channel 50–100 on the 256 channel analyzer. Likewise, the fluorescence signal from the 10 μm particles was centered between channels 10–30 on the 256 channel analyzer. The mean of this reprocessed (see below) fluorescence distribution was taken as the background due to autofluorescence and nonspecific binding of the two sphere types to each other. Then without changing instrument settings or sample flow rates, all tubes in the series were similarly analyzed, as in Example I. All data were computer reprocessed to display only the fluorescence due to single 10 μm particles. To graph the data the means fluorescence background value was subtracted from the mean fluorescence value of each sample in the standard curve and this net fluorescence was plotted as a function of soluble HRP concentration (FIG. 5).

FIG. 5 is that of standard sandwich assay curve. The net fluorescence (mean of the sample minus the mean of the background) is plotted as a function of soluble HRP concentration. Here the assay sensitivity was $10^{-14}$ molar soluble HRP. As cen be seen, the fluorescence intensity increases with increasing HRP concentration. In this Example assay sensitivity was $10^{-14}$ molar soluble HRP. The ability to skip a separation step wherein the unreacted, antigen coated or antibody coated, fluorescent 0.1 μm microspheres would be separated from the 10 μm spheres, allows a quicker and more accurate determination of the results of a binding assay. Sensitivities of $10^{-14}$M in Example II and $10^{-12}$M in Example I were achieved. Previously such sensitivity of measurement could only be obtained, if at all, by radioimmunoassay or enzyme immunoassay techniques. Because the present invention utilizes no radioactive tagging materials, the expense and necessary precautions used when working with radioactive materials can be avoided. Sensitive enzyme immunoassay techniques require separation of phases with the consequent increase in the amount of labor required to perform the techniques.

The foregoing description of the preferred embodiments of the invention have been presented for purposes of illustration and description. It is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A process for the immunochemical determination of the amount of antigen present in a sample comprising the steps of:
    a. providing a known quantity of spheres with antibody coating;
    b. providing a quantity of smaller spheres with an antigen coating, said antigen being the same as the antigen present in said sample, said smaller spheres being fluorescently labeled;
    c. combining said known quantity of spheres with sample and allowing reaction between said antigen in said sample and said antibody on said spheres to occur for a set time period;
    d. combining an excess of said smaller spheres with the mixture of said spheres and said sample produced in step c and then allowing the reactions of antigen in sample and antigen on said smaller spheres with said antibody on said spheres to reach equilibrium;
    e. simultaneously measuring the fluorescence and light scatter of the combined mixture of sample, spheres, and smaller spheres as said combined mixture passes through a flow cytometer equipped with a laser causing the fluorescent chemical in the smaller spheres to fluoresce; and
    f. comparing number and strength of fluorescent events caused by spheres having light scatter measurements within a predetermined range against similar events caused by a spheres reacted with a sample of known antigen concentration.

2. The process of claim 1 wherein said sample and said excess of smaller spheres are added simultaneously to said spheres, and the antigen in said sample and on said smaller spheres is allowed to react with the antibody on said spheres until equilibrium is reached.

3. The process of claim 1 wherein the spheres are 10 μm in diameter.

4. The process of claim 3 wherein the smaller spheres are 0.1 μm in diameter.

5. The process of claim 1 wherein the spheres are composed of latex.

6. The process of claim 1 wherein the antigen is horseradish peroxidase and the antibody is high avidity, anti-HRP antibody.

7. The process of claim 1 wherein the flow cytometer is equipped with a argon-ion laser.

8. A process for the determination of the amount of antigen molecules present in a sample comprising the steps of:
  a. providing a known quantity of spheres and an excess of smaller spheres, both coated with an antibody, said smaller spheres being fluorescently labeled;
  b. combining said known quantity of spheres with sample and allowing reaction between said antigen contained in the molecules of said sample and said antibody on said spheres to occur for a set time period;
  c. combining an excess of said smaller spheres with the mixture of said spheres and said sample produced in step b, and then allowing the reaction of said antibody on said spheres and said smaller spheres with the antigen contained in the molecules in said sample to reach equilibrium;
  d. simultaneously measuring the fluorescence and light scatter of the combined mixture of sample, spheres, and smaller spheres as said combined mixture passes through a flow cytometer equipped with a laser causing the fluorescent chemical in the smaller spheres to fluoresce; and
  e. comparing number and strength of fluorescent events caused by spheres having light scatter measurements with in a predetermined range against similar events caused by spheres with no fluorescent smaller spheres present.

9. The process of claim 8 wherein said sample and said excess of smaller spheres are added simultaneously to said spheres, and the reactions of said antigen with both the antibody on said smaller spheres and the antibody on said spheres are allowed to reach equilibrium simultaneously.

10. The process of claim 8 wherein the spheres are 10 μm in diameter.

11. The process of claim 8 wherein the smaller spheres are 0.1 μm in diameter.

12. The process of claim 8 wherein the spheres are composed of polystyrene latex.

13. The process of claim 8 wherein the antigen is horseradish peroxidase and the antibody is high avidity, anti-HRP antibody.

14. The process of claim 8 wherein the flow cytometer is equipped with an argon-ion laser.

15. A process for the determination of the amount of a binding reactant present in a sample comprising the steps of:
  a. providing a known quantity of synthetic particles with a coating of binder,
  (b). providing a quantity of smaller synthetic particles with a coating of binder reactant, said binder reactant being the same as the binder reactant present in the sample, said smaller particles being fluorescently labeled;
  c. combining said particles with sample and allowing the binding reaction to occur for a set time period,
  d. combining an excess of smaller particles with the mixture of said particles and sample produced in step c and then allowng the binding reactions of the binder on the particles with the binding reactant on the smaller particles and the binding reactant in the sample to both reach equilibrium;
  e. simultaneously measuring the fluorescence and light scatter of the combined mixture of sample, particles, and smaller particles as said combined mixture passes through a flow cytometer equipped with a laser causing the fluorescent chemical in smaller particles to fluoresce; and
  f. comparing number and strength of fluorescent events caused by particles having a light scatter measurement with a predetermined range against similar events caused by particles reacted with a sample of known binder reactant percentage.

16. The process of claim 15 wherein the binding reactant is a ligand and the binder is a receptor for said ligand.

17. The process of claim 15 wherein the binder is an enzyme and the binding reactant is the substrate for said enzyme.

18. The process of claim 15 wherein the binding reactant is a hapten and the binder is an antibody for said hapten.

* * * * *